(12) United States Patent
Smith et al.

(10) Patent No.: US 6,758,850 B2
(45) Date of Patent: Jul. 6, 2004

(54) INSTRUMENTS AND METHODS FOR FLEXION GAP ADJUSTMENT

(75) Inventors: Bryan J. Smith, Ft. Wayne, IN (US); Douglas A. Dennis, Littleton, CO (US); Matthew Smith, Akron, IN (US)

(73) Assignee: DePuy Orthopaedics, Inc., Warsaw, IN (US)

( * ) Notice: Subject to any disclaimer, the term of this patent is extended or adjusted under 35 U.S.C. 154(b) by 70 days.

(21) Appl. No.: 10/109,935

(22) Filed: Mar. 29, 2002

(65) Prior Publication Data

US 2003/0187452 A1 Oct. 2, 2003

(51) Int. Cl.$^7$ .................................................. A61F 5/00
(52) U.S. Cl. ........................... 606/88; 606/87; 606/102
(58) Field of Search .............................. 606/86, 87, 88, 606/89, 90, 102

(56) References Cited

U.S. PATENT DOCUMENTS

| | | | |
|---|---|---|---|
| 4,040,130 A | 8/1977 | Laure | |
| 4,229,840 A | 10/1980 | Gristina | |
| 4,501,266 A | 2/1985 | McDaniel | |
| 4,524,766 A | 6/1985 | Petersen | |
| 4,738,254 A | 4/1988 | Buechel et al. | |
| 5,314,485 A | 5/1994 | Judet | |
| 5,507,821 A | 4/1996 | Koch et al. | |
| 5,540,696 A | 7/1996 | Booth, Jr. et al. | |
| 5,562,675 A | 10/1996 | McNulty et al. | |
| 5,669,914 A | 9/1997 | Eckhoff | |
| 5,683,397 A | 11/1997 | Vendrely et al. | |
| 5,688,279 A | 11/1997 | McNulty et al. | |
| 5,720,752 A | 2/1998 | Elliott et al. | |
| 5,735,904 A | 4/1998 | Pappas | |
| 5,800,438 A | * 9/1998 | Tuke et al. | 606/90 |
| 5,830,216 A | 11/1998 | Insall et al. | |
| 5,908,424 A | 6/1999 | Bertin et al. | |
| 5,911,723 A | 6/1999 | Ashby et al. | |
| 5,911,724 A | 6/1999 | Wehrli | |
| 6,022,377 A | 2/2000 | Nuelle et al. | |
| 6,056,756 A | 5/2000 | Eng et al. | |
| 6,057,756 A | 5/2000 | Eng et al. | |
| 6,077,270 A | 6/2000 | Katz | |
| 6,096,043 A | 8/2000 | Techiera et al. | |
| 6,258,095 B1 | 7/2001 | Lombardo et al. | |
| 6,290,704 B1 | 9/2001 | Burkinshaw et al. | |

FOREIGN PATENT DOCUMENTS

| | | |
|---|---|---|
| EP | 0 327 249 A | 8/1989 |
| FR | 2673100 | 8/1992 |

\* cited by examiner

Primary Examiner—Cary E. O'Connor
Assistant Examiner—Candice C. Melson
(74) Attorney, Agent, or Firm—Maginot Moore & Beck (57) ABSTRACT

A flexion gap instrument is configured to mate with a ligament tensioning tool, such as known distraction devices and pivoting knee balancers. The instrument facilitates making A/P resections in the femur for placement of a femoral prosthesis component to maintain an optimum symmetric flexion gap, which will avoid the risk of medial or lateral laxity in flexion, instability of articulating component dislocation. The instrument includes a base that is configured to sit within the ligament tensioning device, and a vertically extending upstanding portion that is configured to mate with a cutting block or other knee arthroplasty instrument that must be positioned relative to the distal end of the femur. The upstanding portion includes a measurement plate that bears a scale indicating a flexion gap distance. The scale can be used to orient and align the cutting block in its proper position relative to the distal end of the femur, and to orient the cutting block parallel with the tibial plateau with the ligaments properly and equally tensed. In certain embodiments, a leaf spring can be incorporated into the upstanding portion to help support the cutting block and provide a mechanism for temporarily positioning the cutting block on the flexion gap instrument without the need for additional or supplemental locks.

29 Claims, 4 Drawing Sheets

INSTRUMENTS AND METHODS FOR FLEXION GAP ADJUSTMENT

BACKGROUND OF THE INVENTION

Present invention relates to systems and method for reconstructing a femoral portion of a knee in preparation for a total knee replacement. More particularly, the invention relates to systems and methods for orienting a cutting block used to resect portions of the femur, and more specifically in such as way as to balance medial and lateral collateral ligament tension.

Figure 1:
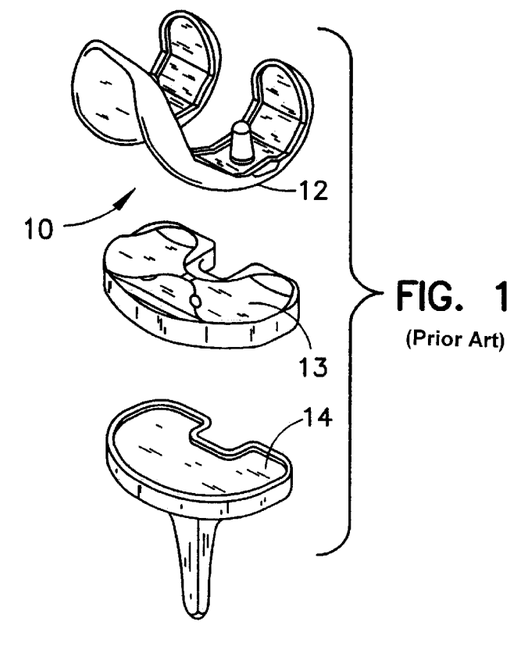
FIG. 1 is an exploded perspective pictorial view of a typical knee prosthesis.

The typical total knee arthroplasty includes three components, as depicted in FIG. 1. In particular, the knee prosthesis 10 includes a femoral component 12, a spacer 13, and a tibial component 14. The design of the components of the knee prosthesis 10 is complicated by the fact that the natural knee does not operate like a hinge moving about a single axis. The knee exhibits dynamic external rotation of the tibia relative to the femur as the knee moves from its flexed to its fully extended position. This automatic rotation of the tibia occurs in the opposite direction when the knee is flexed from its fully extended position to produce an internal rotation of the tibia relative to the femur.

Thus, the natural knee exhibits a rotary laxity that allows the tibia to rotate through a limited arc of both internal and external motion at every degree of knee flexion. While the configuration of the components 12–14 themselves is important to achieve proper knee motion, the specific placement of these components is also critical. Most particularly, the proximal/distal and anterior/posterior positions of the femoral component 12 are critical for duplicating the kinematics of the knee. Much literature and clinical study has been devoted to determining the proper orientation of the prosthesis components, and particularly the femoral component 12.

Figure 2:
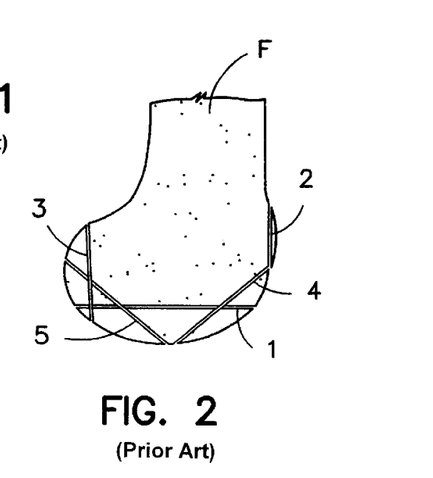
FIG. 2 is a side view of the distal end of a femur illustrating the various cuts made to prepare the femur for a femoral component of the prosthesis shown in FIG. 1.

As is known in the field of total knee arthroplasty, and as can be discerned from FIG. 1, the femoral component 12 exhibits a three-dimensional saddle configuration. The interior of the component is configured to mate with a prepared end of the femur. For the typical femoral component, the orthopaedic surgeon must make five cuts at the proximal end of the femur, as illustrated in FIG. 2. In a typical procedure, a distal cut 1 is made across the distal end of the femur F. The anterior-to-posterior (A/P) placement of the femoral component is determined by the anterior and posterior cuts 2 and 3, respectively. Once those cuts are complete, angled chamfer cuts 4 and 5 are typically made to help secure the femoral component 12 solidly in place. In order to effectively and accurately make these resections, orthopaedic surgeons will typically use a cutting block or cutting guide that is temporarily affected to the distal end of the femur F.

One important factor in determining the proper position of the femoral component, and therefore the proper location for the various cuts 1–5, is the tension in the adjacent soft tissues, particularly the collateral ligaments. Proper tension in the collateral ligaments prevents sideways toggle of the leg. In addition, the collateral ligaments help to limit anterior/posterior travel of the femur relative to the tibia. The spacer 13 (FIG. 1) is an important component for maintaining the proper tension in the collateral ligament. With respect to a prosthetic knee, such as the prosthesis 10, the spacer 13 is necessary to account for the gap that occurs between the distal end of the femur F and the proximal end of the tibia, after portions of both bone ends have been resected.

Figure 3:
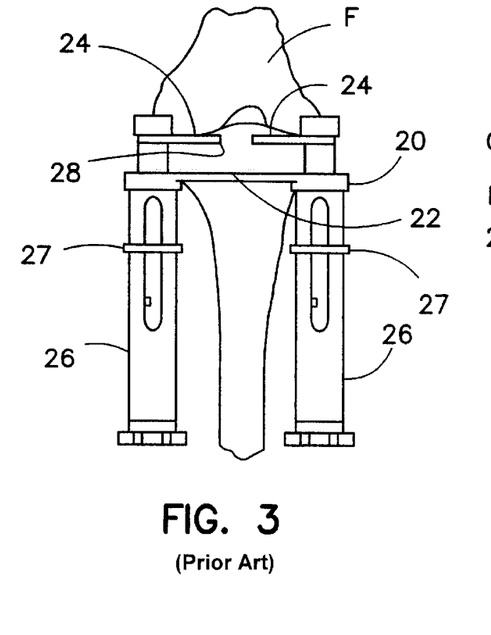
FIG. 3 is a front view of an extended knee joint with a known distraction device operating on the joint.
Figure 4:
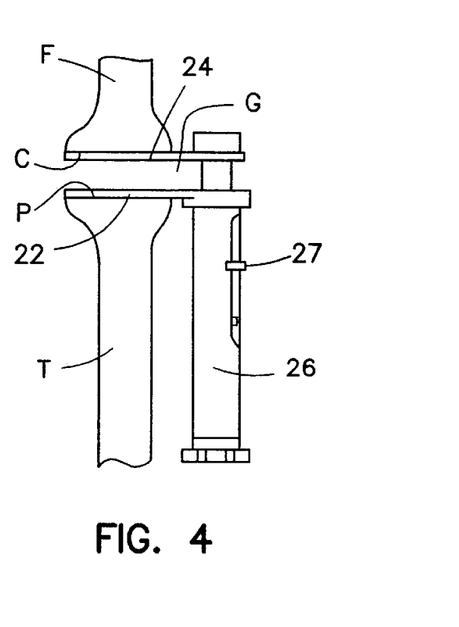
FIG. 4 is a side view of the knee and the distraction device shown in FIG. 3.
Figure 5:
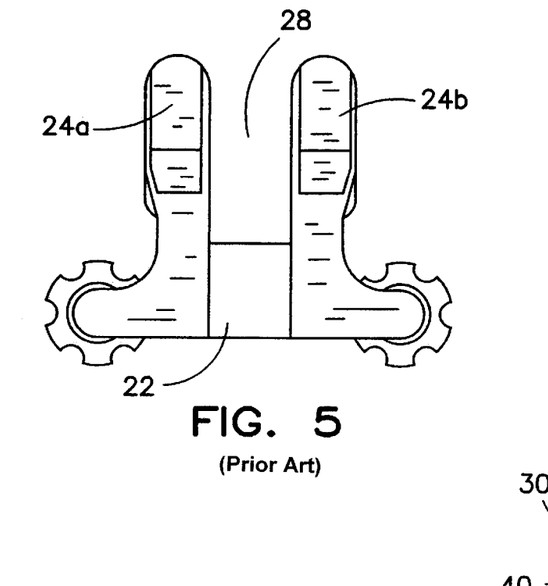
FIG. 5 is a top elevational view of the typical distraction device shown in FIGS. 3 and 4.

Knee instruments have evolved that provide means for mechanically distracting the knee joint to exert the proper tension on the ligaments during the knee arthroplasty procedure. One such instrument is illustrated in FIGS. 3–5. In particular, a distraction device 20 can include a lower member 22 that is adapted to contact the tibia plateau P (FIG. 4) of the tibia T. The distraction device also includes an upper member 24 that contacts the distal end of the femur F, preferably after the first distal cut (cut 1 in FIG. 2) has been performed. With this type of distraction device, the upper member 24 includes a medial and a distal member 24a and 24b, respectively, as depicted in FIG. 5. A pair of parallel adjusting members 26 adjust the position of the two upper members 24a, b relative to the lower member 22. Preferably, the adjusting members 26 operate independently so that the medial upper member 24a can be adjusted differently from the distal member 24b. This independent adjustability of the medial and distal members allows the surgeon to properly orient the mechanical axis of the knee joint relative to the leg bones. Each adjusting member 26 can include an indicator 27 which provides an indication of the joint space, and ultimately the amount of tension applied to the ligaments. The distraction device 20 can be of a variety of types. For the purposes of illustrating the preferred embodiment of the present invention, a distraction device such as the device described in U.S. Pat. No. 4,501,266, issued Feb. 26, 1985, can be implemented. The details of this devise set forth in the '266 Patent are incorporated herein by reference.

In a typical knee arthroplasty procedure, the ligament tension is evaluated with the knee joint in its extended position—i.e. with the femur F and tibia T in alignment. In this position, the prepared surfaces of the femur and tibia are distracted apart by an extension gap G. The ligament tension can be corrected by releasing soft tissue attachments if a medial-lateral imbalance exists, thereby producing a symmetric or parallel extension gap. With this approach, the remainder of the arthroplasty procedure is geared toward maintaining this extension gap.

However, this approach does not account for proper tensioning of the knee when it is in flexion—i.e., when the knee joint is bent. It is with this type of movement that the A/P position of the femoral component 12 is most critical. If the component is offset incorrectly in the A/P direction, the flexion gap will not be correct and will not generate the proper amount of tension in the collateral ligaments. Thus, while the "extension gap first" approach generally assures a proper extension gap, this same approach does not translate to insuring a proper flexion gap. If the flexion gap is incorrect, the ligaments may be too loose or too tight, or the range of motion of the knee may be limited. In addition, poor tensioning in flexion can led to improper femoral rotation, condylar lift-off, accelerated wear of the prosthesis components, and even spin-out or dislocation of the femoral-tibial articulation. It is therefore important to derive a proper A/P position for the femoral component 12.

Some procedures exist which begin with evaluating the flexion gap and then utilizing this flexion gap as the benchmark for the sizing and positioning of the knee prosthesis components. An approach of this type is shown in U.S. Pat. No. 6,056,756, issued May 2, 2000. While the system and method in '756 Patent correlates to the flexion gap, the A/P placement of the femoral component is made with reference to bony land marks on the femur, and not with reference to the flexion gap itself. Moreover, the approach in '756 Patent makes no account for a proper extension gap, except to the extent that sizing of the prosthesis components relative to the flexion gap achieves similar results when the knee is in extension.

Consequently, there is a need for an instrument and technique that more accurately locates the femoral component on the prepared distal end of the femur. This need is particularly acute with respect to the A/P placement of the femoral component, which is ultimately a function of the resection cuts made in the distal end of the femur (see FIG. 2). Thus, the need extends to providing an instrument and method for accurately orienting and positioning the cuts that need to be made in the femur to achieve a properly sized femoral component.

SUMMARY OF INVENTION

To address these needs, the present invention contemplates a flexion gap instrument that is configured to mate with a ligament tensioning tool, such as known distraction devices and pivoting knee balancers. The instrument allows A/P positioning of a cutting block or other knee arthroplasty device to produce a proper flexion gap in the reconstructed knee.

In one embodiment of the invention, the flexion gap instrument includes a base that is configured to sit within the ligament tensioning device, and a vertically extending upstanding portion that is configured to mate with a cutting block or other knee arthroplasty instrument that must be positioned relative to the distal end of the femur. The upstanding portion in one embodiment is an I-beam upstanding portion formed by a back plate and a forward measurement plate. The measurement plate can include a scale or other marker indicating a flexion gap distance which can be used to orient and align the cutting block in its proper position and orientation relative to the distal end of the femur. In a preferred embodiment, the vertically extending upstanding portion is substantially perpendicular to the base. The upstanding portion is arranged so that the supported cutting block is oriented to the cut tibia while the ligaments are tensed to create a symmetric (balanced medial-lateral) flexion gap.

In certain embodiments, a leaf spring can be incorporated into the I-beam to help support the cutting block and provide means for temporarily positioning the cutting block on the flexion gap instrument without the need for additional or supplemental locks. In other embodiments, the vertical extending upstanding portion is in the form of a T-shape for slidable positioning within a correspondingly shaped channel in a cutting block. An alternative feature of the invention contemplates placing the measurement plate at a non-perpendicular angle relative to the base to accommodate particular cutting block designs and to place the block in a desired orientation relative to the tibia.

One aspect of the invention contemplates a method for calibrating a flexion gap relative to a known extension gap value as part of a knee arthroplasty procedure. This method can include the steps of placing the knee joint in flexion, distracting the knee joint, and then placing an instrument relative to the tibia that includes a scale juxtaposed to the distal end of the femur. The scale denotes a gap dimension between the prepared end of the tibia and a particular location on the prepared end of the femur. In the next step, a position on the scale is located that corresponds to a known gap value. All of these steps occur while maintaining the distraction of the knee joint.

In a preferred embodiment, the gap value corresponds to a pre-determined extension gap value. Thus, in a prior series of steps, the knee can be placed in extension, distracted using the distraction device, and the extension gap measured. This measurement can be located on the scale of the flexion gap instrument to determine a proper flexion gap location. This location on the scale can then be used to orienting a cutting block on the femur with a portion of the cutting block aligned with the located position on the scale corresponding to the known extension gap value. The inventive instrument is used to orient the cutting block parallel to the cut proximal end of the tibia while the ligaments are maintained in tension by a distraction tool. In this way, a flexion gap can be established that does not vary between the medial and lateral aspects.

The inventive method can include means for temporarily supporting the cutting block on the instrument. The cutting block can then be mounted on the femur to make the appropriate proximal and distal cuts of the distal end of the femur.

In certain aspect of the invention, the distraction device can be an independent knee balancer device. In other embodiments, the distraction device is a pivoting knee balancer. With each type of distraction device, the flexion gap instrument can be positioned or mated with the distraction plates of the instrument so as not to interfere with the operation of the distraction device.

In one embodiment of the invention, an instrument for establishing the flexion gap of a knee joint in flexion is provided that comprises a base portion configured for placement relative to the proximal end of the tibia with the knee joint in flexion. The instrument also includes a plate projecting from the base portion that is configured to be juxtaposed relative to the distal end of the femur when the base portion is placed relative to the tibia. In a preferred embodiment, the base is configured to rest directly on the tibial plateau, or within the tibial plateau mating plate of the distraction device or ligament balancing tool.

In one feature of the invention, indicia are carried by the plate to define a gap dimension measured from the proximal end of the tibia. In certain embodiments, at least a portion of the plate bearing said indicia is sized to be slidably received in a channel of a cutting block. The instrument can also include means for supporting the cutting block on said plate. In certain embodiments, this means for supporting can include a leaf spring connected to the plate, with the leaf spring arranged to bear against the channel of the cutting block.

In the preferred embodiment, the plate projects substantially perpendicularly from the base. In other embodiments, adapted for use with different cutting blocks, at least a portion of the plate bearing the indicia is oriented at a non-perpendicular angle relative to the base.

It is one object of the invention to provide an instrument for determining a flexion gap that can be used during a total knee arthroplasty procedure. A primary goal is to produce a prosthetic knee joint that maintains proper ligament tension in both extension and flexion.

One benefit of the present invention is that it provides a means for determining a proper flexion gap when the distal end of the femur is being prepared for the prosthesis. Another benefit is that the inventive instrument and method can be used concurrently with existing distraction devices, without interfering with the function of those devices.

Other objects and benefits of the invention will become apparent from the following written description taken with the accompanying figures.

DESCRIPTION OF THE PREFERRED EMBODIMENTS

For the purposes of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

The present invention contemplates a flexion gap instrument that is configured to mate with a ligament tensioning tool, such as known distraction devices and pivoting knee balancers. The flexion gap instrument includes a base that is configured to sit within the ligament tensioning device, and a vertically extending upstanding portion that is configured to mate with a cutting block or other knee arthroplasty instrument that must be positioned relative to the distal end of the femur. The vertical I-beam in one embodiment can be formed by a back plate and a forward measurement plate. The measurement plate includes a scale indicating a flexion gap distance which can be used to orient and align the cutting block in its proper position relative to the distal end of the femur. In certain embodiments, a leaf spring can be incorporated into the I-beam to help support the cutting block and provide means for temporarily positioning the cutting block on the flexion gap instrument without the need for additional or supplemental locks.

Figure 6:
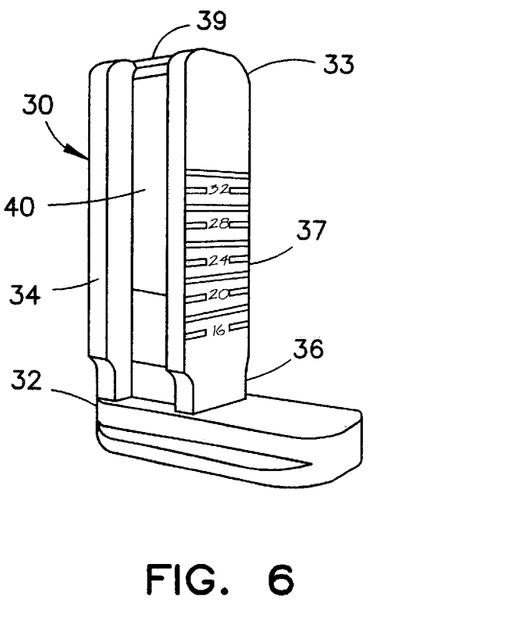
FIG. 6 is a side perspective view of a flexion gap instrument in accordance with one embodiment of the present invention.

The present invention contemplates a flexion gap instrument 30, depicted in FIG. 6. In the illustrated preferred embodiment, the instrument 30 is configured for placement within a ligament tensioning device, such as the distraction device 20 shown in FIGS. 3–5. More specifically, the flexion gap instrument 30 is arranged to fit within the central slot 28 defined between the two medial and distal upper members 24a, 24b. In some embodiments, the lower member 22 can define a portion of the central slot 28 within which the instrument is disposed. In other embodiments, the instrument 30 can be supported on or within the lower member 22.

Figure 7:
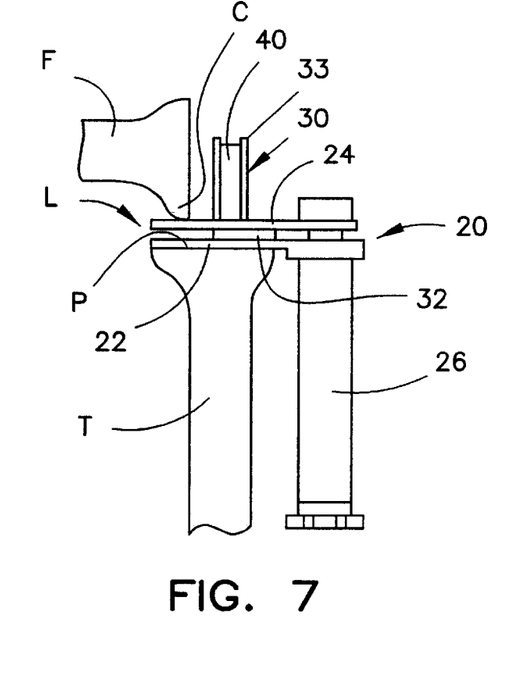
FIG. 7 is a side view, similar to the side view in FIG. 4, showing the flexion gap instrument mounted within the distraction device shown in FIGS. 3 and 4.
Figure 8:
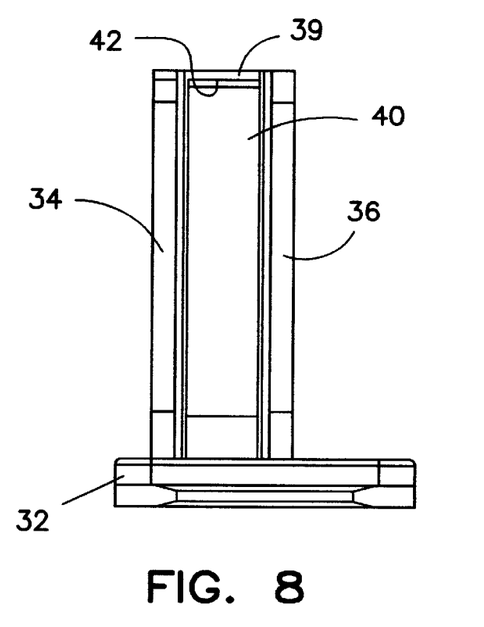
FIG. 8 is a side elevational view of the flexion gap instrument shown in FIG. 6.

Prior to positioning of the flexion gap instrument 30, the femur F can be sized to determine a proper femoral component 12 (FIG. 1). Next, the proximal tibia is resected to form the tibia plateau P (FIGS. 4 and 7). The distal femur can also be cut, such as along the cut line 1 as shown in FIG. 2. In the next step, the soft tissues, and particularly the ligaments, are balanced in extension, as illustrated in FIGS. 3 and 4. Thus, the distraction device 20 can be used to produce an extension gap G. Any imbalance in the soft tissues can be corrected, such as by ligament release. Once the soft tissue surrounding the knee joint has been properly balanced, the extension gap G is sized.

In the next step, the knee is positioned in flexion as shown in FIG. 7. The distraction instrument 20 can be maintained in position as the tibia is moved to its flexed position, or the distraction device can be removed and then repositioned once the knee joint is in flexion. In the flexed position, the lower member 22 is positioned on the tibial plateau P, while the upper members 24a, b contact the posterior condyles C. The ligament balancing tool, or the distraction device 20, is adjusted so that the medial and lateral soft tissues are tensed an amount equal to that arising when the extension gap was evaluated. Thus, in this position, the distraction device 20 will generate a preliminary flexion gap L between the posterior condyles C and the tibial plateau P.

With the knee joint in flexion, and the distraction device in the position shown in FIG. 7, the flexion gap instrument 30 can be positioned within the slot 28 of the distraction device 20. As shown in FIG. 6, the flexion gap instrument 30 includes a base 32 which can be configured to fit tightly within the slot 28 and contact the tibial plateau engaging plate of the distraction device. Alternatively, the lower surface of the base 32 can be configured to rest directly against the tibial plateau P. It is important that the base be positioned parallel to the tibial plateau whether resting on the bone or on the distraction device. In the illustrated preferred embodiment, an upstanding portion 33 projects generally perpendicularly from the base 32. It is important that the upstanding portion 33 be situated perpendicular in the coronal or medial-lateral plane to position the cutting block parallel to the cut tibia while the ligaments are tensed. As shown in FIG. 7, with the knee flexed to 90°, this upstanding portion 33 extends generally parallel to the distal end of the femur F, and perpendicular to the tibial plateau P.

Figure 9:
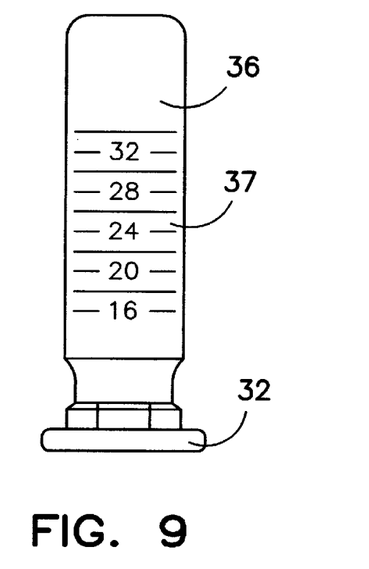
FIG. 9 is a front elevational view of the flexion gap instrument shown in FIGS. 6 and 8.

The upstanding portion 33 can be of an I-beam upstanding portion and can include a back plate 34 that directly faces the femur, and a forward measurement plate 36. The measurement plate 36 includes a scale 37 or similar scale markings thereon to provide a visual indication of dimension. More specifically, the scale 37 provides markings corresponding to different gap dimensions. In the illustrated embodiment, these gap dimensions can commence at 16 mm, which corresponds to a distance of 16 mm from the scale marking to the bottom of the tibial plateau engaging plate of the distraction device or ligament balancing device. Alternatively, the scale markings can be calibrated to the bottom surface of the base 32. In addition, in the illustrated embodiment, the scale markings can be set at dimensions of 16, 20, 24, 28, and 32 mm, with intermediate 2 mm markings, as best shown in FIG. 9.

The base 32 can have a length that is less than the length of the slot 28 in the distraction device 20. This permits the flexion gap instrument 30 to slide fore and aft relative to the prepared end of the distal femur F. In another aspect of the preferred embodiment, the upstanding portion 33 is offset to one end of the base 32. The scale markings, such as scale 37 can be included on the back face of the back plate 34, as well as on the front face of the measurement plate 36. With this configuration, the instrument 30 can be associated with the distraction device in two orientations that allows the vertical measurement scale to be positioned closer to or further away from the distal end of the femur. In certain uses, the instrument can be initially placed in one orientation to measure the flexion gap, such as with the back plate 34 juxtaposed to the femur, and then repositioned or rotated 180° so that the upstanding portion is offset from the distal femur for supporting a cutting block.

In one method of use, the flexion gap instrument is initially position as shown in FIG. 7 set apart from the condyles C of the femur F. With the distraction device 20 and the flexion gap instrument 30 in this position and with the knee in flexion, a cutting block, such as the cutting block 45 shown in FIG. 10, can be positioned for mounting on the instrument 30. The cutting block 45 can be of a variety of types. In the illustrated embodiment, the cutting block 45 includes an interior channel 46 that is sized to receive the flexion gap instrument 30 therein. The cutting block also includes a lower alignment edge 48 that is used with the present invention to define the flexion gap. As shown in FIG. 11, the cutting block 45 can also include fixation pins 50 that are used to temporarily fix the cutting block to the distal end of the femur while the particular bone resections are being made. The block can also include a number of cutting guides 52 in the form of slots sized for receiving known resection saws or osteotomes.

The flexion gap instrument is positioned over the proximal end of the tibia so that the measurement scale 37 is juxtaposed to the proximal end of the femur. In other words, the scale 37 is oriented so that it provides a direct visual relationship of the gap indicia to the end of the femur. Preferably, the knee joint is flexed to 90° so that the condyles C, or more appropriately the distal cut 1 (see FIG. 2) made in the femur, is generally perpendicular to the tibial plateau. With this orientation, the measurement plate 36 of the instrument 30 will be generally parallel with the prepared end of the femur, to allow accurate A/P positioning of the ancillary devices relative to the femur.

In some instances, the cut 1 in the distal end of the femur can be at an angle relative to the end plane of the condyles. In these instances, when the knee is flexed to the preferred 90° orientation, the prepared end of the femur is not perpendicular to the prepared tibial plateau. In order accommodate this modified angle, the upstanding portion 33 can be oriented at a non-perpendicular angle relative to the base 32. In this way, the upstanding portion can be juxtaposed to the angled surface of the femur to provide an accurate flexion gap measurement and parallel positioning of the cutting block relative to the distal end of the femur.

As shown in FIG. 11, the cutting block 45 is mounted over the flexion gap instrument 30, with the instrument disposed within the interior channel 46 of the block. The block is positioned so that its alignment edge 48 is aligned with a particular value or indicator on the scale 37 of the measurement plate 36. In accordance with one aspect of the present inventive method, the extension gap G is measured when the knee is in extension as shown in FIGS. 3 and 4. The cutting block 45 is then arranged with its aligned edge 48 pointing to the particular value measured for the extension gap G. For instance, if the extension gap G is measured at 22 mm, then the alignment edge 48 of the cutting block 45 can oriented at the 22 mm line on the scale 37 of the instrument 30.

In accordance with this illustrated embodiment, the cutting block 45 can be positioned so that the flexion gap value is the same as the extension gap value G. This similarity relies upon the uniform thickness of the femoral component 12 in its posterior and medial presentation. Of course, if the femoral component exhibits different a geometry, in particular different thicknesses in these two orientations, the actual flexion gap value would be adjusted to account for this difference in thickness. However, for the purposes of the present invention, it is assumed that the femoral component 12 is uniform so that the extension gap value G can be used to establish a correct flexion gap that generates the optimum and correct amount of tension in the ligaments in both flexion and extension. Once the alignment edge 48 of the cutting block has been properly positioned, the cutting block 45 can be secured to the distal end of the femur F and the appropriate bone resections can be made.

In the preferred embodiment, the upstanding portion 33 is perpendicular to the tibial plateau in the sagittal plane of the knee. Thus, the rotational position of the cutting block in the plane parallel to the distal end of the femur will be controlled so that the cutting block will be substantially parallel to the tibial plateau. Proper rotational positioning of the cutting block helps ensure correct rotational positioning of the femoral prosthesis.

It should be appreciated that the flexion gap instrument 30 primarily provides a means for accurately determining the proper flexion gap so that the knee joint exhibits the same stability and flexion as it does in extension. In addition, it should also be appreciated that the instrument 30 allows the cutting block 45 to be positioned while the knee joint is being actively distracted and the surrounding soft tissues maintained in their accustomed tension. This approach ultimately ensures accurate A/P and rotational positioning of the cutting block, which leads to accurate cuts in the femur, and ultimately to optimum A/P and rotational positioning of the femoral component 12.

Figure 10:
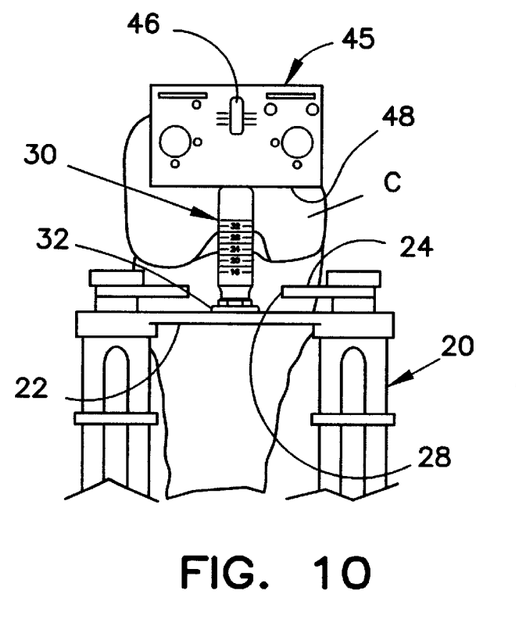
FIG. 10 is a front view of a knee in flexion with the flexion gap instrument of one embodiment of the present invention supported within a distraction device, such as the device shown in FIGS. 3 and 4, and with one type of cutting block shown in a position prior to mounting on the flexion gap instrument.
Figure 11:
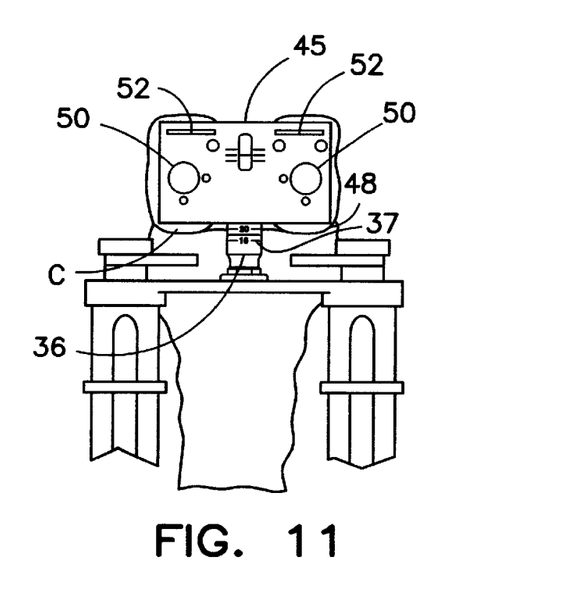
FIG. 11 is a front view similar to the view of FIG. 10 with the cutting block shown positioned over the flexion gap instrument of the present invention.

As illustrated in FIGS. 10 and 11, the cutting block 45 is slid over the end of the I-beam upstanding portion 33 of the flexion gap instrument 30. This cutting block 45 includes an interior channel 46 into which the instrument 30 is received. In a preferred embodiment of the invention, the instrument 30 includes a web 39 spanning between the back plate 34 and the measurement plate 36 that helps insure stability of the two plates. In addition, the web can support a leaf spring 40 between the two plates 34 and 36. This leaf spring can exert moderate spring pressure against the interior of the cutting block 45 which can be sufficient to support the cutting block independently on the flexion gap instrument 30. Thus, this temporary support eliminates the need for any temporary fixation, such as bone pins extending through apertures in the cutting block.

In one specific embodiment, the leaf spring 40 can include leaf components on either side of the web 39 that project outwardly from that web. The spring can pass through a slot 42 defined at the upper end of the web 39 to help retain the leaf spring 40 in position. As an alternative, the spring element 40 can be arranged to exert a distracting force against the inside of the back plate 34 and the measurement plate 36. With this approach, the two plates would be nominally pushed apart by the spring 40 so that the plates would exert a friction force against the interior of the cutting block channel 46. With either approach, the cutting block 45 can be temporarily supported by the flexion gap instrument 30 until the fixation pins 50 are properly positioned within the distal end of the femur F.

The flexion gap instrument 30 in accordance with the present embodiment of the invention can be used with a variety of tensioning devices and cutting blocks. For instance, shown in FIG. 12, the flexion gap instrument 30 is shown supporting a cutting block 55 of a slightly different upstanding portion than the cutting block 45 illustrated in FIGS. 10 and 11. In this instance, the cutting block includes an alignment notch 56 defined at the lower end of the cutting block. This notch can be used to read the flexion gap values from the scale 37 on the flexion gap instrument 30.

Figure 12:
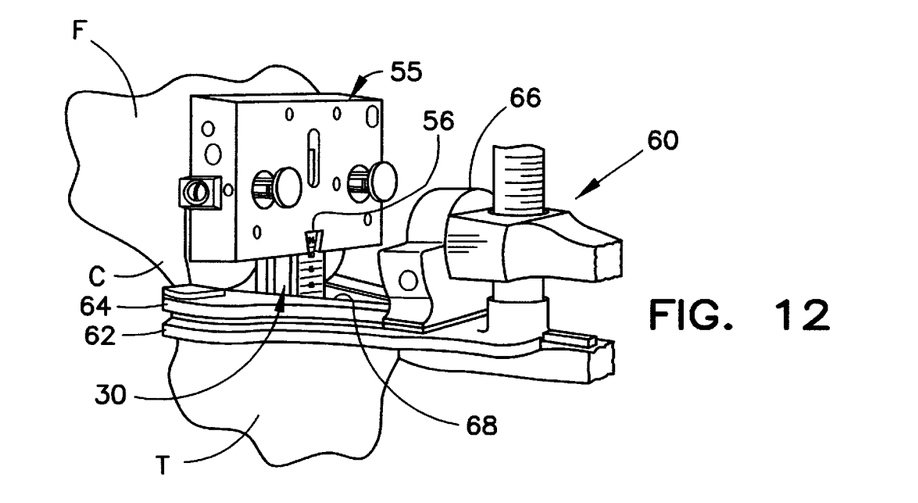
FIG. 12 is a side perspective view of the use of one embodiment of the flexion gap instrument in connection with a known pivoting knee balancer.

In addition, as depicted in FIG. 12, the instrument 30 can be mated with a pivoting knee balancer 60. The knee balancer 60 can be of a variety of known upstanding portions. As with the distraction device 20, the knee balancer 60 includes a lower member 62 configured to contact the prepared end of the tibia, and a pair of upper members 64 that contact the condyles of the femur F. The upstanding portion and use of a pivoting knee balancer 60 of this type is well known. The balancer includes an adjusting member 66 that permits adjustments in the spacing and angular orientation of the upper member 64 relative to the lower member 62. Like the distraction device 20, the pivoting knee balancer 60 provides a slot 68 between the upper members 64 and defined in the lower member 62. Thus, the flexion gap instrument 30 can be readily disposed within that slot when the pivoting knee balancer 60 is in its operative position maintaining tension in the soft tissues surrounding the knee joint.

Figures 13, 14, 15:
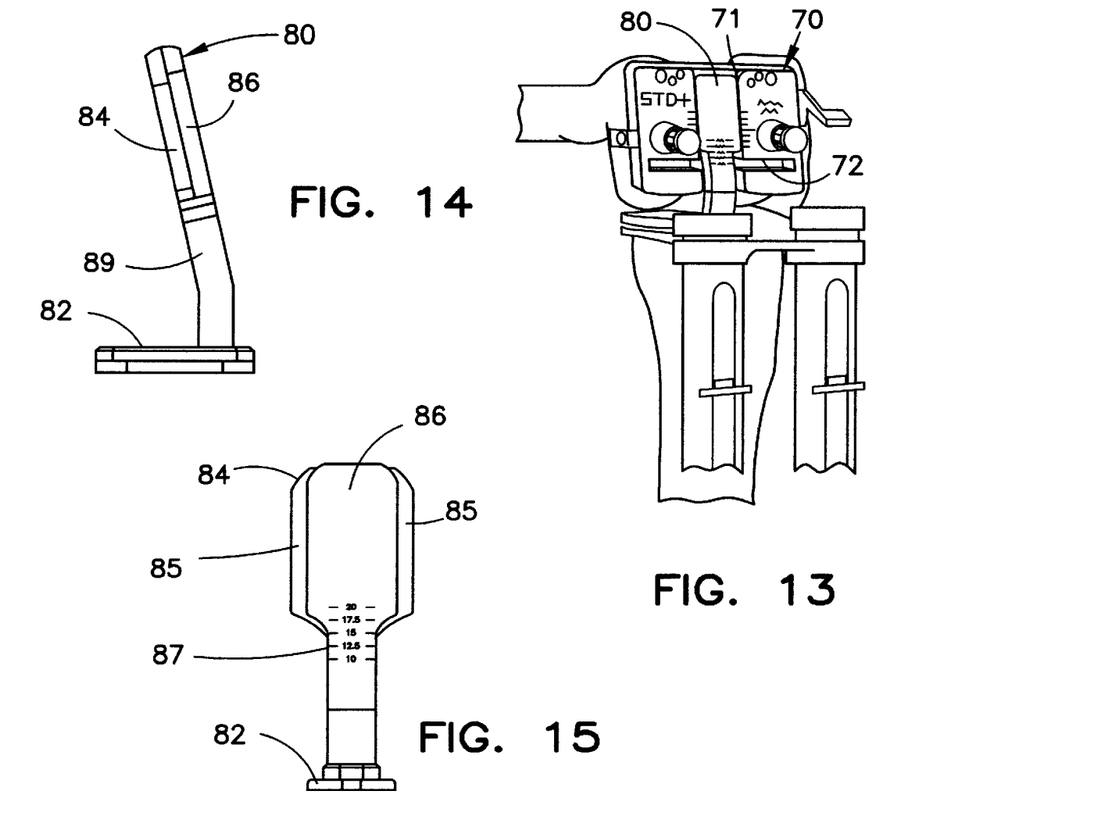
FIG. 13 is a front prospective view of a flexion gap instrument in accordance with an alternative embodiment of the present invention, shown in use in connection with a known distraction device and a known cutting black.
FIG. 14 is a side view of the flexion gap instrument shown in FIG. 13.
FIG. 15 is a front view of the flexion gap instrument shown in FIG. 14.

Other known cutting blocks have different upstanding portions from the cutting block 45 and 55 illustrated and discussed above. For example, as shown in FIG. 13, a cutting block 70 includes an open channel 71. In accordance with certain known cutting blocks, the central channel 71 exhibits a t-shape. The block 70 also defines an open cutting guide 72 or slot that is arranged and sized to receive a cutting saw or osteotome.

In accordance with a further embodiment of the present invention, a flexion gap instrument 80, shown in FIGS. 14 and 15, can be provided for use with this type of cutting block. Specifically, the instrument 80 includes a base 82 that can be similar to the base 32 of the flexion gap instrument 30. The instrument 80 also includes a back plate 84 that faces the femur F, and a forward facing measurement plate 86. As shown in the figures, the back plate 84 and measurement plate 86 are integral of each other, with the back plate defining a flange 85 around the side edges of the measurement plate 86. Thus, the back plate and measurement plate form a "T" that is configured to be slidably received within the similarly shaped central channel 71 of the cutting block 70. As with the flexion gap instrument 30, the instrument 80 includes a scale 87 defined on the measurement plate 86, which provides a visual indication of the measured flexion gap. The appropriate measurement on the scale 87 can be read by aligning the upper edge of the cutting guide 72 in the cutting block 70 with the appropriate scale value.

In another aspect of this invention, the flexion gap instrument 80 can include an angled arm 89 supporting the back plate and measurement plate on the base 82. This configuration of the flexion gap instrument 80 can accommodate a particular configuration of cutting block, such as the cutting block 70. Since the scale 87 is on the measurement plate 86 that is angled away from the perpendicular to base 82, the measurement values on the scale must be adjusted accordingly. However, the use of the flexion gap instrument 80 can proceed as described above with respect to the flexion gap instrument 30. The angle of the arm 89 can also be dictated by whether the prepared distal end of the femur is at an angle relative to the perpendicular, as discussed above.

The measurement plates 36, 86 of the respective flexion gap instruments 30, 80 have a length that is sufficient to support the different cutting blocks therein. Moreover, the length of the measurement plates must be sufficient to accommodate a corresponding scale 37, 87 that is capable of a wide range of gap measurements. In a preferred embodiment, the plates have a length of about 2.5 inches measured from the bottom face of the base 32, 82. With this preferred embodiment, the top of the plate will reach the anterior condyles of the femur for a normally distracted knee joint.

The flexion gap instruments of the present invention are preferably formed of a medical grade metal, such as stainless steel. However, since the instruments do not bear any substantial load, they can be formed of an alternative material, such as a medical grade plastic.

It can be appreciated that the present invention contemplates an instrument that is well-suited for an "extension gap first" knee arthroplasty approach. Once the extension gap has been evaluated, the instrument, such as instrument 30 or 80, can be utilized with the knee joint in flexion to properly calibrate the flexion gap. The flexion gap instrument of the present invention is especially useful for aligning a cutting block in the A/P direction to make accurate cuts in the condyles.

The instrument 30 or 80 can be easily used with the knee distraction or ligament tensioning device in its operative position without interfering with the function of the distraction/tensioning device. Moreover, the instruments 30 or 80 provide a clear visual indication of a proper flexion gap to allow accurate positioning of the cutting block or other instrumentation associated with the knee arthroplasty procedure. For instance, the instrument can be used to align a template for positioning fixation pins or for creating an intramedullary bore.

While the invention has been illustrated and described in detail in the drawings and foregoing description, the same should be considered as illustrative and not restrictive in character. It is understood that only the preferred embodiments have been presented and that all changes, modifications and further applications that come within the spirit of the invention are desired to be protected.

For example, the flexion gap instrument can be modified to mate with a variety of distraction devices. In the illustrated embodiments, the distraction devices define a slot that receives the base of the flexion gap instrument so that the base can rest on the tibial plateau. The instrument can be modified so that its base rests on the lower plate of the distraction device itself. In this instance, the measurement scale on the flexion gap instrument would need to be modified to account for the thickness of the distraction plate.

What is claimed is:

1. In a knee arthroplasty procedure, a method for calibrating a flexion gap relative to a known extension gap value, comprising the steps of:
   placing the knee joint in flexion;
   distracting the knee joint;
   placing an instrument relative to the tibia that includes a scale juxtaposed to the distal end of the femur, the scale denoting a gap dimension;
   locating a position on the scale corresponding to the known extension gap value while maintaining the distraction of the knee joint; and
   orienting a cutting block on the femur with a portion of the cutting block aligned with the located position on the scale corresponding to the known extension gap value.

2. The method according to claim 1, wherein the step of orienting a cutting block includes temporarily supporting the cutting block on the instrument.

3. The method according to claim 2, wherein the step of orienting a cutting block includes mounting the cutting block on the femur.

4. In a knee arthroplasty procedure, a method for calibrating a flexion gap relative to a known extension gap value, comprising the steps of:
   placing the knee joint in flexion;
   distracting the knee joint;
   placing an instrument relative to the tibia that includes a scale juxtaposed to the distal end of the femur, the scale denoting a gap dimension; and
   locating a position on the scale corresponding to the known extension gap value while maintaining the distraction of the knee joint,
   wherein the distracting step is performed using a distraction device; and
   wherein the step of placing an instrument includes mating the instrument with a portion of the distraction device contacting the tibia.

5. The method according to claim 4, wherein the distraction device is an independent knee balancer device.

6. The method according to claim 4, wherein the distraction device is a pivoting knee balancer device.

7. In a knee arthroplasty procedure, a method for calibrating a flexion gap relative to a known extension gap value, comprising the steps of:
   placing the knee joint in flexion;
   distracting the knee joint;
   placing an instrument relative to the tibia that includes a scale juxtaposed to the distal end of the femur, the scale denoting a gap dimension;
   locating a position on the scale corresponding to the known extension gap value while maintaining the distraction of the knee joint;
   balancing the tension in the ligaments of the knee; and
   maintaining the balanced tension during the placing and locating steps.

8. In a knee arthroplasty procedure, a method for positioning a cutting block on the prepared distal end of the femur, comprising the steps of:
   placing the knee joint in flexion with the prepared distal end of the femur at an angle of at least 90° relative to the tibial plateau;
   distracting the knee joint;
   providing an instrument having a base and an upstanding portion, the upstanding portion configured to support the cutting block;
   while maintaining the knee joint in distraction, placing the instrument relative to the tibial plateau so that the upstanding portion is juxtaposed with the distal end of the femur; and
   placing the cutting block on the upstanding portion with the block aligned with the prepared distal end of the femur.

9. The method according to claim 8, wherein the step of placing the cutting block includes orienting the cutting block so that the block is rotationally aligned on the upstanding portion to be substantially parallel to the tibial plateau.

10. The method according to claim 8, further comprising the step of mounting the cutting block to the prepared distal end in the aligned position.

11. The method according to claim 8, wherein the step of distracting the knee joint includes balancing the medial and collateral ligament tension.

12. The method according to claim 8, further comprising the steps of:
    determining the extension gap; and
    while the cutting block is supported on the upstanding portion of the instrument, aligning the cutting block relative to the prepared distal end of the femur at a distance form the tibial plateau corresponding to the extension gap.

13. The method according to claim 12, wherein the step of determining the extension gap includes:
    distracting the knee joint; and
    balancing the medial and lateral collateral ligament tension.

14. An instrument for establishing the flexion gap of a knee joint in flexion, comprising:
    a base portion configured for placement relative to the proximal end of the tibia with the knee joint in flexion;
    a plate projecting from said base portion and configured to be juxtaposed relative to the distal end of the femur when said base portion is placed relative to the tibia; and
    indicia on said plate defining a gap dimension measured from the proximal end of the tibia,
    wherein said plate is part of an I-beam upstanding portion projecting from said base.

15. The instrument according to claim 14, wherein said plate projects substantially perpendicularly from said base.

16. The instrument according to claim 14, wherein at least a portion of said plate bearing said indicia is oriented at a non-perpendicular angle relative to said base.

17. The instrument according to claim 14, wherein said indicia includes a set of scale markings.

18. The instrument according to claim 14, wherein said plate is part of a T-shaped upstanding portion projecting from said base, said T-shaped upstanding portion sized to be received within a correspondingly shaped channel in a cutting block.

19. The instrument according to claim 14, adapted for use with a distraction device having a lower plate for contacting the tibia and an upper plate for contacting the femur defining a slot therethrough, wherein said base portion is sized for positioning within the slot in the upper slot and engagement with the lower plate.

20. The instrument according to clam 14, wherein said base has opposite ends and said plate projects from said base nearer one of said opposite ends than the other of said opposite ends.

21. The instrument according to claim 14, wherein at least a portion of said plate bearing said indicia is sized to be slidably received in a channel of a cutting block.

22. The instrument according to claim 21, further comprising means for supporting the cutting block on said plate.

23. The instrument according to claim 22, wherein said means for supporting includes a leaf spring connected to said plate, said leaf spring arranged to bear against the channel of the cutting block.

24. An instrument for establishing the flexion gap of a knee joint in flexion, comprising:

a base portion configured for placement relative to the proximal end of the tibia with the knee joint in flexion;

a plate projecting from said base portion and configured to be juxtaposed relative to the distal end of the femur when said base portion is placed relative to the tibia; and indicia on said plate defining a gap dimension measured from the proximal end of the tibia, wherein said instrument is adapted for use with a distraction device having a lower plate for contacting the tibia and an upper plate for contacting the femur defining a slot therethrough, wherein said base portion is sized for positioning within the slot in the upper slot and engagement with the lower plate, and wherein the slot in the distraction device has a length, wherein said base has a length less than the length of the slot in the distraction device.

25. A knee arthroplasty procedure, comprising the steps of:

(a) placing a knee joint in extension;

(b) distracting the knee joint while in extension so as to produce an extension gap;

(c) measuring the extension gap;

(d) placing the knee joint in flexion after step (c);

(e) placing an instrument having a scale relative to the knee joint while in flexion;

(f) distracting the knee joint while in flexion so as to produce a preliminary flexion gap as measured by said scale that corresponds to said extension gap; and (g) resecting a portion of a femur of said knee joint based on said preliminary flexion gap.

26. The procedure of claim 25, wherein:

said instrument includes a base and an upstanding portion, said scale is defined on said upstanding portion, and said instrument placing step includes the step of positioning said upstanding portion in juxtaposition to a distal end of said femur.

27. The procedure of claim 25, further comprising the step of:

(h) moving a tibia of said knee joint in relation to said femur of the knee joint from an extension orientation to a flexion orientation while a distraction device is secured to the knee joint.

28. The procedure of claim 25, wherein said step of distracting the knee joint while in extension includes a first step of balancing medial and collateral ligament tension of the knee joint.

29. The procedure of claim 28, wherein said step of distracting the knee joint while in flexion includes a second step of balancing medial and collateral ligament tension of the knee joint.

* * * * *